United States Patent [19]

Mathews et al.

[11] Patent Number: 5,311,767
[45] Date of Patent: May 17, 1994

[54] INSTRUMENT AND METHOD FOR VISCOELASTICITY MEASUREMENTS

[75] Inventors: Michael Mathews; David G. Rusling; Michael J. Stolc, all of Swindon, England

[73] Assignee: Monsanto PLC, Basingstoke, United Kingdom

[21] Appl. No.: 872,374

[22] Filed: Apr. 23, 1992

[30] Foreign Application Priority Data

Apr. 26, 1991 [GB] United Kingdom ............... 9108961

[51] Int. Cl.⁵ .............................................. G01N 3/24
[52] U.S. Cl. ........................................ 73/843; 73/846
[58] Field of Search ................ 73/846, 847, 843, 841, 73/54.39

[56] References Cited

U.S. PATENT DOCUMENTS

| | | | |
|---|---|---|---|
| 4,337,646 | 7/1982 | Fraleigh . | |
| 4,552,025 | 11/1985 | Barker et al. | 73/846 |
| 4,584,882 | 4/1986 | Tosaki | 73/847 |
| 5,079,956 | 1/1992 | Burhin et al. | 73/54.39 X |
| 5,163,317 | 11/1992 | Ono et al. | 73/54.39 X |

FOREIGN PATENT DOCUMENTS 0041375 9/1981 European Pat. Off. .
0057566 8/1982 European Pat. Off. .

OTHER PUBLICATIONS

American Society for Testing and Materials (1990) (ASTM) D1646-89 vol. 9, pp. 307-314 (310).
IBM Technical Disclosure Bulletin vol. 31, No. 2, Jul. 1988, New York, US, p. 61, "Modified Technique for Using an Oscillating Shearing Disk Viscometer".

Primary Examiner—Hezron E. Williams
Assistant Examiner—Joseph W. Roskos
Attorney, Agent, or Firm—Gordon B. Seward

[57] ABSTRACT

The invention relates to an instrument and method for measuring the viscoelastic properties of rubber and like materials comprising two opposed dies, each die having a die housing, the dies and housings being moveable between an open position and a closed position, and wherein: a) each die is separated from its housing by a substantially uniform circumferential gap such that the die is rotatable relative to its housing, and one die is rotatable relative to the other, b) in the closed position, the two dies define between them a cavity for holding under pressure a sample of material to be tested, c) the design of the dies and housings is such that during movement from the open position to the closed position, a sample of test material located between the dies is compressed so that excess material is extruded radially from between the dies, across the gap between each die and its housing and through a narrowing space separating the housings until the two housings reach their closed position, in which position the said space is sealed. The radial dimension of the gap between each die and its housing is significantly less than in prior art instruments, and sheets of film of heat and distortion-resistant material are used to bridge the gaps.

6 Claims, 1 Drawing Sheet

INSTRUMENT AND METHOD FOR VISCOELASTICITY MEASUREMENTS

The present invention relates to an instrument and method for measuring the viscoelastic properties of rubber and like materials. More particularly, the invention relates to such an instrument having two opposed dies adapted to contain between them under pressure a sample of material to be tested, means to apply an oscillatory torque to one of said dies, means for measuring the torque thereby induced in the other die and means for deriving information on the properties of the material from such measurements.

In a typical instrument, each die is, in general terms, a circular disc rotatable in a co-axial cylindrical housing surrounding the die, and there is at least one annular seal of heat-resistant elastomeric material seated in a groove in an axially-extending face of the die or housing and in contact with an adjacent axially-extending face of the housing or die respectively. Such seals are required to maintain a constant pressure on the sample during the test. The use of such seals has disadvantages, however. For example, wear of the seal during use means that the instrument requires periodic recalibration during the life of a seal and eventual replacement of the seal. Examples of such instruments are described in GB-A-1247371, U.S. Pat. No. 4,552,025 and U.S. Pat. No. 4,584,882.

The instrument and method of the present invention does not require this type of seal. In effect, a new seal is provided in a simple and effective manner for each test sample. An instrument of the invention comprises two opposed dies each having a co-axial die housing, the dies and housing being moveable between an open position and a closed position and wherein:

(a) each die is separated from its housing by a substantially uniform circumferential gap such that the die is rotatable relative to its housing, and one die is rotatable relative to the other, (b) in the closed position, the two dies define between them a cavity for holding under pressure a sample of material to be tested, (c) the design of the dies and housing is such that during movement from the open position to the closed position, a sample of test material having a volume greater than the volume of the cavity is compressed and the excess is extruded radially from between the dies, across the gap between the dies and their housings and through a narrowing space separating the housings until the two housing reach their closed position in which the said space is sealed by extruded material, and (d) the radial dimension of the circumferential gap between each die and its housing is such that a film of heat-and distortion-resistant material which is substantially non-adherent to the surfaces of the dies and housings can be used to bridge the circumferential gap completely, the strength of the film being such that a the bridge of film resists rupture during closure of the dies and housings with a sample of test material in situ and during testing of the sample. In such an instrument, there is no need for annular seals of the type described above with reference to prior art instruments, between a die and its housing.

The prior art on instruments for viscoelasticity measurements also includes the Mooney viscometer. In connection with this instrument, ASTM D1646 recommends the use of heat-resistant film as a barrier between a sample to be tested and the dies of the viscometer where the sample is a "sticky" compound.

The method of the invention is a method of operating an instrument as described above, which method comprises covering at least the peripheral surface of one die and the adjacent surrounding surface of the die housing with a film of heat and distortion resistant material which is substantially non-adherent to the surfaces of the die and die housing so that the gap between the die and die housing is completely bridged by the film, placing a sample of material to be tested on the film and to cover the die, the sample having a volume greater than the volume of the cavity formed between the first and second dies when in their closed position, placing a second film of the said material between the sample and at least the peripheral surface of the second die and the surrounding surface of the second die housing so that the gap between the second die and housing is completely bridged by the second film, moving the dies and housings towards the closed position, thereby compressing and extruding excess sample material from between the dies and their housings, and through a narrowing space which separates the first and second housings until the first and second housings reach their closed position in which the said space is filled and sealed by extruded material, carrying out the required test, opening the dies and removing the sample and films.

Although it can be envisaged that the films which form bridges between the dies and their housings could be rings, for simplicity of operation in practice, each film will normally be of a size to cover the entire main surface of the die and adjacent surfaces of the housing, so that two films provide linings for at least the die cavity and the space which is filled and sealed by extruded material when the housings are in their closed position.

In prior art instruments having gaps between dies and housings which are adapted to accommodate annular seals within the gaps, the radial dimension of such a gap, i.e. the clearance between the die and the housing, is typical about 2 mm (2000 $\mu$m). In contrast, the clearance between a die and its housing in an instrument of the present invention is significantly less, for example in the range 10-60 $\mu$m, preferably in the range 20-30 $\mu$m.

As indicated above, the invention has particular application in measuring the viscoelastic properties of rubber and like materials. Such measurements are usually made at temperatures significantly above room temperature, for example at temperatures in range 100° to 300° C. or even higher, such as temperatures in the range 150°-250° C. The film used in the present invention should therefore be heat-resistant and substantially retain its integrity at the operating temperature. Tests using the instrument of the invention generally involve the application of an oscillatory torque to one die and measurement of the torque thereby induced in the other die. Some instruments are intended mainly to study the viscoelastic properties of rubber during vulcanisation. For such studies, the angle of oscillation of the first die is comparatively small, for example from ±0.1° to ±1°. Other instruments, for example the rotorless viscometer described in European Patent Application 90870151.9 are designed so that the first die is capable of oscillating through larger angles, for example up to 90°. In the method of the present invention, however, the film needs to be able to withstand the twisting distortion imposed by the relative rotation of the dies. It would be expected, therefore, that the choice of films meeting the necessary criteria would be wider when operating at low angles of oscillation, for example up to ±5°, than when operating at relatively large angles of oscillation.

Various polymer films having non-adhesive and thermal characteristics which make them suitable for use in the present invention are known, for example aromatic polyesters, polyamides and polyimides. Films of various thicknesses can be used. Apart from cost, however, a limitation in this respect is that the film should be pliable and extensible enough to conform accurately to the shape of the surfaces of the dies, for example, the dies in certain instruments are provided with alternating radial ribs and grooves to minimise slipping between the dies and the sample. Overall, however, the selection of a film which is acceptable under a particular set of test conditions and having the required balance of strength and thickness is essentially a matter of simple experimentation, but generally film thickness in the range 15–50 $\mu$m would be expected to be suitable.

Polyester film having a thickness in the range 15–30 $\mu$m, more especially in the range 20–25 $\mu$m, has been found to be particularly suitable, for example, polyester film based on polyethylene terephthalate. Such films typically have a tensile strength at break in the range 175–215 MPa in the machine direction and 225–275 MPa in the transverse direction, a yield stress in the range 85–105 MPa in both directions, and an elongation at break in the range 110–140% in the machine direction and 70–90% in the transverse direction. These values are determined by ASTM method D-882-83 carried out at 23° C., 50% relative humidity and a strain rate of 50%/min.

Certain polyamide, polyimide, mixed polyimide/-polyamide and polyester ether ketone films can also be used, for example, 'Kapton' polyimide film. In addition, metallised polymer films would be expected to be suitable, as well as certain metallic films or foils.

Tests using the instrument and method of the invention have shown that, at least with the preferred polyester films referred to above, the presence of the film lining to the die cavity does not, in most cases, significantly change the results compared with those obtainable in the absence of the film. In other instances, the presence of the film may cause a change in the results, but it is a constant change which can be allowed for by recalibration of the instrument.

In the accompanying drawing.

Figure 1A:
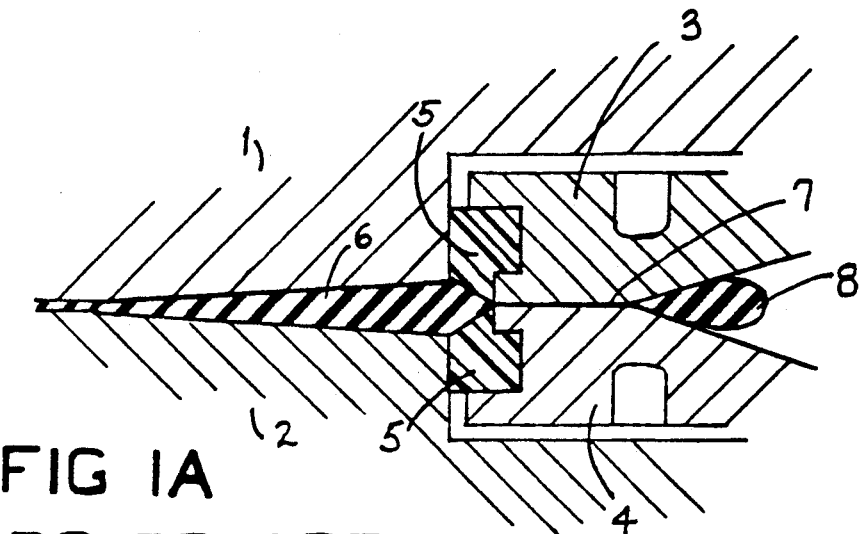
FIG. 1(a) shows a radial cross-section part of the die assembly of a prior art instrument in the closed position.

The die assembly in FIG. 1(a) comprises upper and lower dies (1) and (2) and upper and lower seal plates (3) and (4). The seal plates form part of the die housing, being attached to other components of the die housings in a manner not shown. A sealing ring (5) is positioned between each die and its housing. Excess sample material from the mould cavity (6) is extruded through the space (7) between the die housings during closure of the die assembly, to form a flash (8), the space (7) being filled and sealed by extruded material in the closed position shown. This material together with the sealing rings (5) ensure that a sample in the mould cavity (6) is maintained under pressure during a test.

Figure 1B:
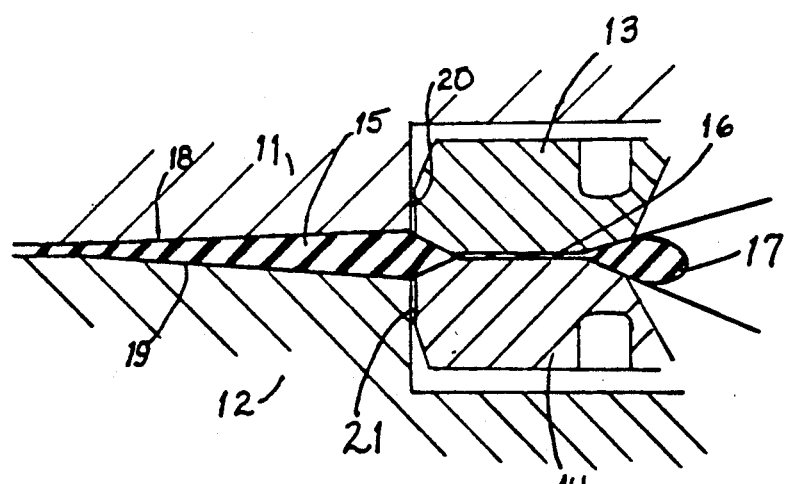
FIG. 1(b) shows a corresponding partial radial cross-section of an instrument according to the invention.

The die assembly in FIG. 1(b) comprises upper and lower dies (11) and (12), and upper and lower seal plates (13) and (14). During closure of the die assembly, excess sample material from the die cavity (15) is extruded through the space (16) to form a flash (17). The die cavity (15) and the space (16) are lined by continuous sheets of film (18) and (19) which bridge the gaps (20) and (21) between the dies (11) and (12) and the corresponding seal plates (13) and (14). The thickness of the film and the size of the gaps are selected so that the bridge of film resists rupture on closure of the die assembly and during a test. The sheets of film (18) and (19) thus together form a pressurisable container for a sample of test material in the die cavity (15), with a peripheral seal being provided by extruded test material which fills the space (16).

We claim:

1. An instrument for measuring the viscoelastic properties of rubber and like materials, comprising two opposed ideas, each die having a die housing, the dies and housings being moveable between an open position and a closed position, and wherein:
   a) each die is separated from its housing by a substantially uniform circumferential gap such that the die is rotatable relative to its housing, and one die is rotatable relative to the other,
   b) in the closed position, the two dies define between them a cavity for holding under pressure a sample of material to be tested,
   c) the design of the dies and housings is such that during movement from the open position to the closed position, a sample of test material located between the dies is compressed so that excess material is extruded radially from between the dies, across the gap between the dies and their housings and through a narrowing space separating the housings until the two housings reach their closed position, when the said space is sealed, characterised in that there is provided a film of heat- and distortion-resistant material which is substantially non-adherent to the surfaces of the dies and die housings, the strength of the film being such that the bridge of film resists rupture during closure of the dies and die housings with a sample of test material in situ and during the subsequent test, the radial dimension of the gap between each die and its housing being such that the film completely bridges the gap, and there being no annular seal within the gap bearing against an axially-extending face of the die and/or die housing.

2. An instrument according to claim 1 wherein the radial dimension of the circumferential gap between a die and its housing is in the range 10–60 $\mu$m.

3. A method of operating an instrument as defined in claim 1, which method comprises covering at least the peripheral surface of one die and the adjacent surrounding surface of the die housing with a film of heat and distortion resistant material which is substantially non-adherent to the surfaces of the die and housing so that the circumferential gap between the die and the housing is completely bridged by the film, placing a sample of material to be tested over the die, the sample having a volume greater than the volume of the cavity formed between the first and second dies when in their closed position, placing a second film of the said material between the sample and at least the peripheral surface of the second die and the surrounding surface of the second die housing so that the circumferential gap between the second die and its housing will be completely bridged by the second film when the dies and housings are closed, moving the dies and housings towards the closed position, thereby compressing and extruding excess sample material from between the dies, between the first and second films and through a narrowing space which separates the first and second housings until the housings reach their closed position in which the said space is sealed by the extruded material, carrying out the required test, opening the dies and removing the sample and films.

4. A method according to claim 3 in which each film is of a size sufficient to cover the entire surface of the die which, in the absence of the film would be in contact with the sample, and to cover adjacent surfaces of the housings, so that the two films provide a lining at least for the die cavity and for the space which is sealed by extruded material when the housings are in their closed position.

5. A method according to claim 3 or claim 4 in which the film has a thickness in the range 10–50 μm and the test is carried out at a temperature not exceeding 300° C.

6. A method according to claim 5 in which the film is based on an aromatic polyester or aromatic polyamide or polyimide and has a thickness in the range 15 to 30 μm, and the test is carried out at a temperature not exceeding 200° C.

* * * * *